(12) United States Patent
Altermann et al.

(10) Patent No.: US 12,201,815 B2
(45) Date of Patent: *Jan. 21, 2025

(54) DEVICE FOR ADMINISTERING A FLUID

(71) Applicant: Intervet Inc., Madison, NJ (US)

(72) Inventors: Frank Altermann, Tuttlingen (DE); Dominic Kamenzin, Eigeltingen-Reute (DE); Thomas Schmidt, Tuttlingen (DE); Manuel Mattes, Spaichingen (DE); Robin Sauter, Tuttlingen (DE); Daniel Seeh, Immendingen (DE)

(73) Assignee: INTERVET INC., Rahway, NJ (US)

( * ) Notice: Subject to any disclaimer, the term of this patent is extended or adjusted under 35 U.S.C. 154(b) by 40 days.

This patent is subject to a terminal disclaimer.

(21) Appl. No.: 18/057,636

(22) Filed: Nov. 21, 2022

(65) Prior Publication Data

US 2023/0158240 A1 May 25, 2023

Related U.S. Application Data

(63) Continuation-in-part of application No. 17/040,415, filed as application No. PCT/EP2019/057535 on Mar. 26, 2019, now Pat. No. 11,534,550.

(30) Foreign Application Priority Data

Mar. 26, 2018 (DE) .......................... 102018107102.7

(51) Int. Cl.
*A61M 5/30* (2006.01)
*A61M 5/31* (2006.01)
*A61M 5/315* (2006.01)

(52) U.S. Cl.
CPC .......... *A61M 5/30* (2013.01); *A61M 5/31501* (2013.01); *A61M 5/31511* (2013.01);
(Continued)

(58) Field of Classification Search
CPC ............... A61M 5/30; A61M 5/31501; A61M 5/31511; A61M 5/31528
See application file for complete search history.

(56) References Cited

U.S. PATENT DOCUMENTS 3,057,349 A 10/1962 Aaron
3,353,537 A 11/1967 Knox et al.
(Continued)

FOREIGN PATENT DOCUMENTS

DE 4436540 A1 4/1996
JP 6509954 A 11/1994
(Continued)

*Primary Examiner* — Bradley J Osinski
(74) *Attorney, Agent, or Firm* — Keith O'Doherty; Jenny Cromsigt

(57) ABSTRACT

A device for administering a fluid is provided, with a cylinder (16, 116) which has an open dispensing end (17), a piston (36) which is displaceable between a front and rear end position in the cylinder (16, 116) and is connected to a piston rod (35) that protrudes along a first direction beyond a rear end of the cylinder (16, 116) opposite the open dispensing end (17) and is guided in a receiving block (10), a nonreturn valve (18) closing the open dispensing end (17),
and a tensioning device (S) which is connected to the piston rod (35, 135) and is arranged in the receiving block (10). The tensioning device (S) has a ramp (52) which is rotatable by means of a motor (12) and has a ramp track (53) extending along a helical line, wherein the ramp track (53) ascends from a first plateau along a region of inclination (S1, S2) to a second plateau and descends from the second plateau to the first plateau via a transition flank (46).
The tensioning device (S) furthermore has a roller (51) which is in contact with the ramp track (53) and is mounted rotatably in a driver (50), which is connected to that end of the piston rod (35, 135) which protrudes out of the cylinder
(Continued)

(16, 116), and therefore, upon rotation of the ramp (52), the ramp track (53) runs below the roller (51), which thereby rotates, wherein the roller (51) has a support region (55) which rests on the region of inclination (S1, S2) of the ramp track (53), and at least one laterally adjoining side region (56, 57) which has a smaller outside diameter than the support region (55) and which does not rest on the region of inclination (S1, S2) of the ramp track (53), wherein, during rotation of the ramp, both the support region (55) and the side region (56, 57) come into contact with an edge (54) of the ramp track (53), said edge connecting the second plateau to the transition flank (46).

19 Claims, 8 Drawing Sheets

(52) U.S. Cl.
CPC . *A61M 5/31528* (2013.01); *A61M 2005/3114* (2013.01); *A61M 2005/3128* (2013.01)

(56) References Cited

U.S. PATENT DOCUMENTS

| | | |
|---|---|---|
| 3,973,697 A | 8/1976 | Crum et al. |
| 4,103,684 A | 8/1978 | Ismach |
| 8,647,305 B2 | 2/2014 | Ohta et al. |
| 2011/0224613 A1 | 9/2011 | D'Antonio et al. |
| 2012/0010576 A1 | 1/2012 | Raab |

FOREIGN PATENT DOCUMENTS

| | | |
|---|---|---|
| JP | 2002539857 A | 11/2002 |
| JP | 2013153849 A | 8/2013 |
| JP | 2015506248 A | 3/2015 |
| WO | 1993003779 A1 | 3/1993 |
| WO | 2000056381 A1 | 9/2000 |
| WO | 2005072795 A2 | 8/2005 |
| WO | 2007140610 A1 | 12/2007 |
| WO | 2008063995 A2 | 5/2008 |
| WO | 2013117659 A2 | 8/2013 |

DEVICE FOR ADMINISTERING A FLUID

CROSS-REFERENCE TO RELATED APPLICATIONS

This application is a continuation application of U.S. application Ser. No. 17/040,415, filed Sep. 22, 2020, which is a national stage entry under 35 U.S.C. § 371 of PCT/EP2019/057535 filed on Mar. 26, 2019, which claims priority to DE102018107102.7 filed on Mar. 26, 2018, the content of PCT/EP2019/057535 is hereby incorporated by reference in its entirety.

FIELD OF THE INVENTION

The present invention relates to a device for administering a fluid, which device can be in the form of, for example, a self-filling syringe without a needle, with which a liquid drug can be administered to animals.

BACKGROUND OF THE INVENTION

Such devices for administering a fluid are intended to be as lightweight as possible, to have a long service life and to be associated with low maintenance costs and outlay.

It is the object of the invention to provide a device for administering a fluid that realizes at least one of the properties mentioned.

The invention is defined in claim 1. Advantageous refinements are specified in the dependent claims.

SUMMARY OF THE INVENTION

The device according to the invention for administering a fluid comprises a cylinder which has an open dispensing end, a piston which is displaceable between a front and a rear end position in the cylinder and is connected to a piston rod that protrudes along a first direction beyond a rear end of the cylinder opposite the open dispensing end and is guided in a receiving block, a nonreturn valve (or intake valve) closing the open dispensing end, and a tensioning device which is connected to the piston rod and is arranged in the receiving block. The tensioning device can move the piston rod in a tensioning operation, when the piston is in its front end position, along the first direction until the piston is in its rear end position, in order thereby to fill the cylinder with the fluid to be administered and in order to pretension the piston rod toward the open dispensing end. Furthermore, the tensioning device, when the piston is in its rear end position, can release the piston rod in a dispensing operation, and therefore the piston moves counter to the first direction as far as its front end position because of the applied pretension and, in the process, the fluid in the cylinder is dispensed via the nonreturn valve for administering.

The administering device according to the invention furthermore has a ramp which is rotatable by means of the motor and has a ramp track extending along a helical line. The ramp track ascends from a first plateau or level along a region of inclination to a second plateau or second level and descends from the second plateau to the first plateau via a transition flank. The ramp track therefore has a single turn and may be referred to as being helical with a step.

The tensioning device furthermore comprises a roller which is in contact with the ramp track and is mounted rotatably in a driver, which is connected to that end of the piston rod which protrudes out of the cylinder, and therefore, upon rotation of the ramp, the ramp track runs below the roller, which thereby rotates. The roller is preferably mounted in such a manner that its axis of rotation is perpendicular to the first direction (or perpendicular to the longitudinal axis of the piston rod).

For the tensioning operation, the ramp track, starting from contact of the roller with the first plateau, can be rotated in such a manner that the roller runs on the region of inclination as far as the second plateau and the piston is thereby moved into its rear end position. For the dispensing operation, the ramp track, starting from a contact of the roller with the second plateau, can be rotated until the roller via the transition flank reaches the first plateau and the piston is thereby moved into its front end position.

The distance of the second plateau from the first plateau along the axis of rotation of the ramp preferably corresponds to the distance from the front to the rear end position of the piston along the first direction and therefore to the piston stroke.

The rotational movement of the motor is therefore converted by means of the ramp and the roller into a translatory movement of the piston rod along its longitudinal axis. The administering device can therefore be tensioned by means of the motor, and therefore a user merely has to actuate a triggering element, for example a pushbutton, a switch, a rocker switch or a button, in order to release the dispensing operation and therefore to administer the fluid. It is therefore possible, for example, for many animals to be rapidly injected one after another with medication.

In the case of the administering device according to the invention, the roller has a support region which rests on the region of inclination of the ramp track, and at least one laterally adjoining side region which has a smaller outside diameter than that of the support region and which does not rest on the region of inclination of the ramp track. During the dispensing operation, both the support region and the side region can come into contact with an edge of the ramp track, said edge connecting the second plateau to the transition flank. This leads to the advantage of there being a relatively low rolling or frictional resistance between the roller and the ramp track in the region of the region of inclination. During the transfer via the edge for the dispensing operation, both the receiving region and the side region then rest on the edge, and therefore the support surface is enlarged here, and thus a smaller pressure is present. This is advantageous since, during the transfer of the roller via the edge, the greatest force acts on the roller, and therefore undesirable pressure peaks can be reduced. The durability of the roller is therefore increased.

In particular, the roller on either side of the support region can have a laterally adjoining side region with a smaller outside diameter than that of the support region. This leads to a further reduction of the pressure on the roller during the transfer via the edge.

The roller can be designed in such a manner that the outside diameter of the support region is constant. The outside diameter of the respective side region can decrease in a direction toward the side of the roller (or in a direction away from the support region or as the distance from the support region becomes greater).

The roller can be in the form of a plastics roller. The ramp can be composed of metal.

The region of inclination of the ramp track can have a first portion adjoining the first plateau and an adjoining second portion, wherein the inclination of the second portion is greater than the inclination of the first portion.

The effect is therefore advantageously achieved that, at the beginning of the tensioning operation, the ramp track has a smaller inclination, as a result of which the motor has to apply less force or torque. This is advantageous during the starting of the motor since more current is used during the starting. As soon as the first portion merges into the second portion, said starting problem has been overcome, and therefore a greater inclination can easily be realized here. This increases the durability of the motor.

The region of inclination of the ramp track can be designed in such a manner that both portions are linear with respect to the angle of rotation of the screw. However, it is also possible for the first portion and/or the second portion to have a nonlinear profile with respect to the angle of rotation. In this case, the inclination of the respective portion is preferably the average inclination of the respective portion. The nonlinear profile of the respective portion is preferably a profile in which the local inclination increases as the angle of rotation increases. The nonlinear profile of the respective portion can preferably be a concave curvature profile.

In particular, the rotational angle region (or the length of the angle of rotation) of the first portion can be smaller than the rotational angle region (or the length of the angle of rotation) of the second portion. The ratio of the rotational angle region of the first portion to the rotational angle region of the second portion is preferably no more than 4/6 and not less than 1/9.

The cylinder together with the nonreturn valve can be in the form of an exchangeable front assembly, which may also be referred to as an exchangeable assembly, which is releasably connected to the receiving block.

The entire front assembly which is subject to the greatest amount of wear during the operation of the device for administering a fluid (preferably a liquid) can then be changed into a new (preferably structurally identical) front assembly which is then connected to the receiving block. The durability of the entire device for administering a fluid is therefore significantly increased.

The exchangeable assembly can be arranged at the front end of the device according to the invention. In particular, for example, during correct use of the device according to the invention part of the exchangeable assembly can be in contact with the animal to which the fluid is intended to be administered. In this respect, at least this part of the exchangeable assembly protrudes from the rest of the device according to the invention. The exchangeable assembly can have a part which forms the distal end of the device according to the invention, and therefore, for example, for this reason the exchangeable assembly may also be referred to as an exchangeable front assembly.

An exchangeable front assembly is understood here as meaning in particular that the front assembly as a whole can be separated from the receiving block and replaced by a structurally identical front assembly which is connected for exchange to the receiving block. However, it is also possible for the front assembly which is separated from the receiving block to be maintained (by, for example, worn parts, such as seals, being exchanged) and then being connected again to the receiving block.

Since the front assembly is completely separated from the receiving block and is then maintained or exchanged, undesirable contaminations can be reliably avoided. This is significantly more difficult and associated with higher costs if, for example, only the firstly wearing O-ring seals in the front assembly are exchanged individually when the front assembly, as previously customary, is installed in such a manner that it cannot be separated from the rest of the administering device without being destroyed.

The releasable connection between the front assembly and the receiving block can be in particular, a screw connection. However, any other type of releasable connection, such as, for example, a bayonet connection, is also possible.

The administering device according to the invention can have a nozzle for administering the fluid without a needle, said nozzle being connected via the nonreturn valve to the open dispensing end of the cylinder and being part of the front assembly. It is therefore possible for the nozzle also to be exchanged at the same time as the front assembly is exchanged.

Alternatively, the device can have a needle or canula which is connected via the nonreturn valve to the open dispensing end of the cylinder and is part of the front assembly. The needle and the canula may for their part be exchangeable.

The administering device according to the invention can have precisely one cylinder with precisely one piston rod and precisely one front assembly. However, it is also possible for the administering device to have two or more cylinders with two or more piston rods and two or more front assemblies that are all designed identically, and therefore two or more identical or different fluids can be admitted simultaneously. The individual cylinders can have identical or different volume.

The administering device according to the invention is in particular in the form of a self-filling administering device which uses the tensioning operation to enable the cylinder to be filled with the fluid to be administered (for example a liquid to be administered).

This can be realized, for example, in such a manner that filling of the cylinder already takes place during the entire tensioning operation. Alternatively, the administering device can be designed in such a manner that, during the tensioning operation, a negative pressure is built up in the cylinder, said negative pressure then being used, when the piston is in its rear end position, for the fluid to be sucked into the cylinder because of the negative pressure. For this purpose, for example, the distal end of the piston can have a blind hole which extends in the longitudinal direction of the piston rod and from which one or more radial bores branch off, the radial bores, in the rear end position of the piston, producing a fluid connection to a reservoir of the fluid to be administered.

The administering device according to the invention can have the motor which is used for carrying out the tensioning operation. It may also be stated that the motor provides the energy necessary for building up the pretensioning of the piston rod. The motor can be mounted, in particular on the receiving block.

In order to operate the motor and possible further consumers, the energy source provided can be, for example, a battery and/or a storage battery. The energy source can be formed, for example, in the base or as the base of the administering device. Furthermore, the energy source can be exchangeable or fixedly installed.

The tensioning device can have a spring which pretensions the piston rod toward the open dispensing end when the piston is in the rear end position.

In the case of the administering device according to the invention, the receiving block can be in the form of an integral receiving block which is produced by an additive production method.

Such an additive production method may also be referred to as 3D printing and may be, for example, a laser sintering method.

This leads to the receiving block being able to be produced with a relatively low weight and high rigidity and strength. The overall weight of the administering device is therefore kept as low as possible, thus making the operation thereof for a user agreeable and durable.

Furthermore, the integral formation of the receiving block by means of the additive production method leads in an advantageous manner to it being possible for the receiving block to be formed extremely compactly, which is not possible with conventional machining production methods.

The material used for the receiving block is preferably a metal (or a metal alloy) and, in particular, titanium, and therefore the receiving block is composed of metal (or a metal alloy) and in particular of titanium. Furthermore, aluminum, steel (for example maraging steel), stainless steel, titanium, a nickel alloy and/or a cobalt chromium alloy can be used as material for the receiving block. Further possible materials are AlSiMg alloys, CoCrMo alloys and nickel chromium alloys. Furthermore, materials which are weldable can be used. All of these materials can be present in a form (for example as powder) in order to able to produce the receiving block from them by means of an additive production method (and in particular by means of the laser sintering).

The receiving block can have a motor bearing, a guide cylinder for the piston rod, at least one receptacle for a control board, a receptacle for a fluid connection for a fluid container and/or at least one housing fixing point, which is/are formed integrally with the receiving block.

The piston can be formed integrally with the piston rod. In this case, the front end of the piston rod forms the piston. However, it is also possible for the piston to be a separate element that is connected to the piston rod.

It goes without saying that the features mentioned above and those which have yet to be explained below are usable not only in the stated combinations, but also in other combinations or by themselves without departing from the scope of the present invention.

The invention will be explained in more detail below using exemplary embodiments with reference to the attached drawings which likewise disclose features essential to the invention. These exemplary embodiments serve merely for illustrative purposes and should be interpreted as restrictive. For example, a description of an exemplary embodiment with a multiplicity of elements or components should not be interpreted to the effect that all of said elements or components are necessary for implementation purposes. On the contrary, other exemplary embodiments may also contain alternative elements and components, fewer elements or components or additional elements or components. Elements or components of various exemplary embodiments may be combined with one another, unless stated otherwise. Modifications and alterations that are described for one of the exemplary embodiments may also be applied to other exemplary embodiments. In order to avoid repetitions, identical or mutually corresponding elements in the various figures are denoted by the same reference signs and will not be explained repeatedly. In the figures:

DETAILED DESCRIPTION OF THE INVENTION

Figure 1:
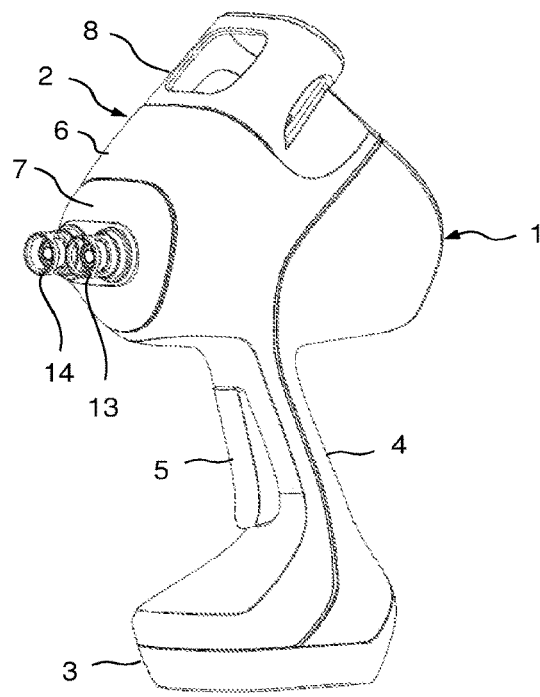
FIG. 1 shows a perspective view of an exemplary embodiment of the administering device 1 according to the invention.

In the exemplary embodiment shown in FIG. 1, the device 1 according to the invention for administering a fluid (for example a liquid) comprises a housing 2 which comprises a base 3, which can also be in the form of a standing base 3, a gripping portion 4 for holding the device 1, a trigger 5 which is arranged in the gripping portion 4 and is intended for actuating the device 1, a head region 6 with a dispensing region 7, and a receptacle 8 in the upper end of the head region 6.

In the exemplary embodiment described here, the device 1 according to the invention, which may also be referred to as the administering device 1, is designed for simultaneously administering two different drugs in animals, wherein the administration of the drug is carried out through the skin without needles.

In the case of the administering device 1 according to the invention, a separate cylinder-piston arrangement is provided for each medication, as will also be described in detail below, said cylinder-piston arrangement being in each case in the form of a type of self-filling device in such a manner that a movement of the piston toward the dispensing end causes the fluid to be injected and an opposite movement of the piston causes filling of the cylinder for the next injection operation.

Figure 2:
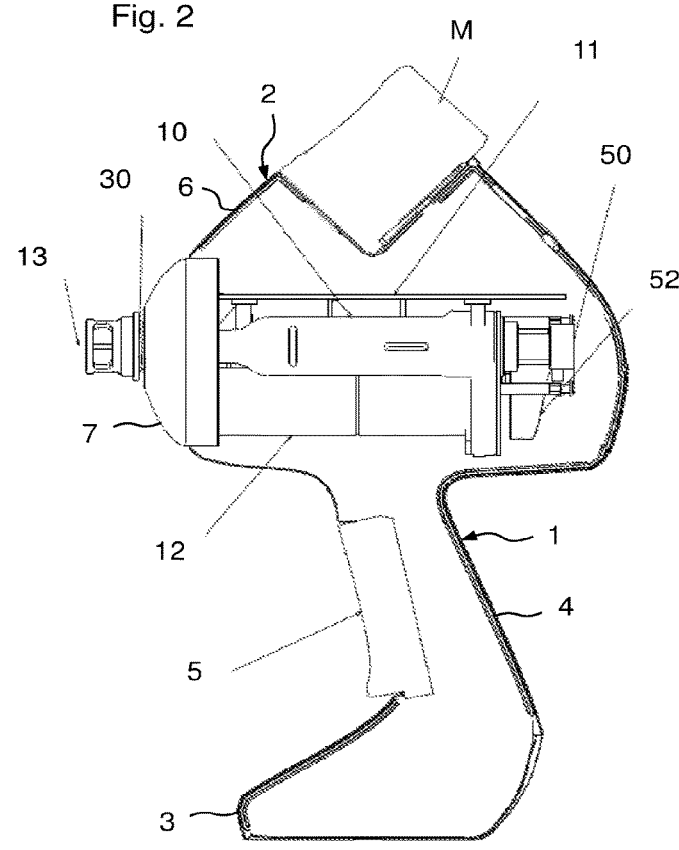
FIG. 2 shows a schematic sectional view of the administering device 1 from FIG. 1.

As can be inferred from the schematic sectional illustration of the administering device 1 in FIG. 2, the administering device 1 comprises a receiving block 10 which bears a control board 11 and a motor 12, and two front assemblies 13, 14, of which only the front assembly 13 is visible in the illustration of FIG. 2. Since the front assemblies 13 and 14 are constructed identically, essentially only the front assembly 13 will be described in detail below. A medication container M containing a liquid drug for the front assembly 13 is shown schematically in the receptacle 8.

Figure 3:
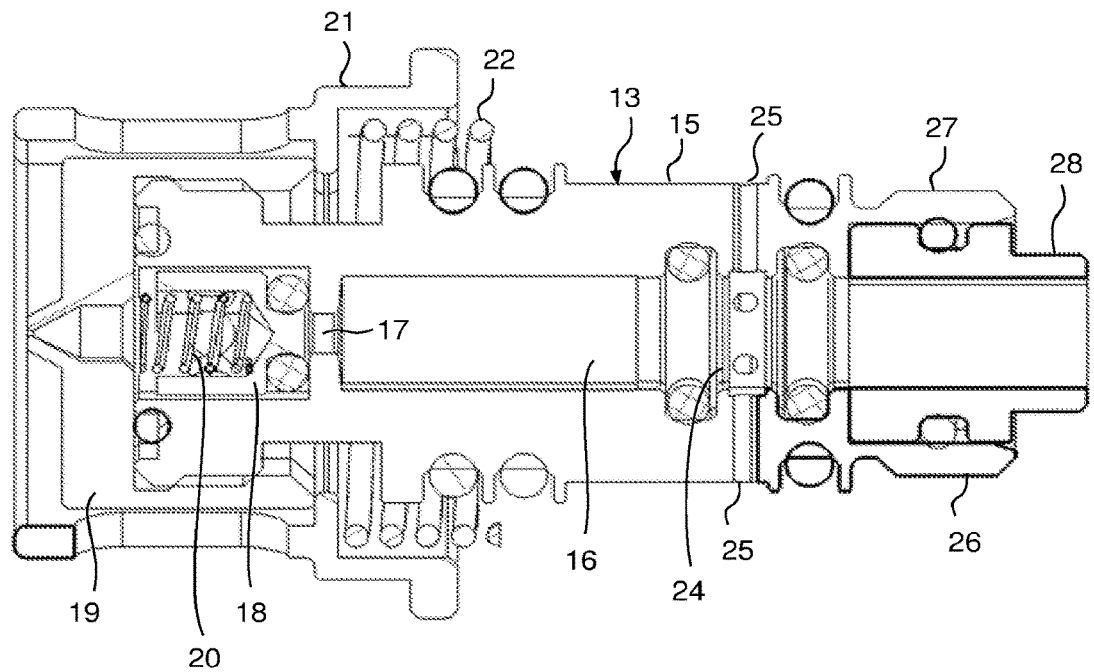
FIG. 3 shows a schematic, enlarged sectional view of the first front assembly 13.

A sectional illustration of the front assembly 13 is shown in FIG. 3. The front assembly 13 comprises an insert 15 in which a syringe cylinder 16 with an open dispensing end 17 is formed. A nonreturn valve 18 (or an intake valve 18) is arranged on the outlet side at the open dispensing end 17. When the nonreturn valve 18 is opened, the open dispensing end 17 leads into a nozzle 18 via which the fluid to be dispensed (here the corresponding liquid drug) is dispensed.

The nonreturn valve 18 is pretensioned via a spring 20 toward the open dispensing end 17 and closes the open dispensing end 17 in the position of the nonreturn valve 18 that is shown in FIG. 3.

Furthermore, the front assembly 13 comprises a triggering cage 21 which extends over the nozzle 19, is pressed by means of a spring 22 in the direction from the open dispensing end 17 toward the nozzle 19 and is pretensioned. The triggering cage 21 is mounted displaceably along the longitudinal axis of the front assembly 13 (from the left to the right in FIG. 3), and therefore, when the administering device 1 is placed onto the corresponding skin site of the animal, said triggering cage is displaced in the direction from the nozzle 19 toward the open dispensing end 17 and, in the process, triggers, for example, a contact sensor (not shown) which enables the triggering of the administering operation, as will also be described in detail below.

The insert 15 has radially running supply channels 25 at a proximal end 24 of the syringe cylinder 16 lying opposite the open dispensing end 17, via which supply channels the fluid to be administered or the liquid drug passes into the syringe cylinder 16 for a next injection operation.

Figure 4:
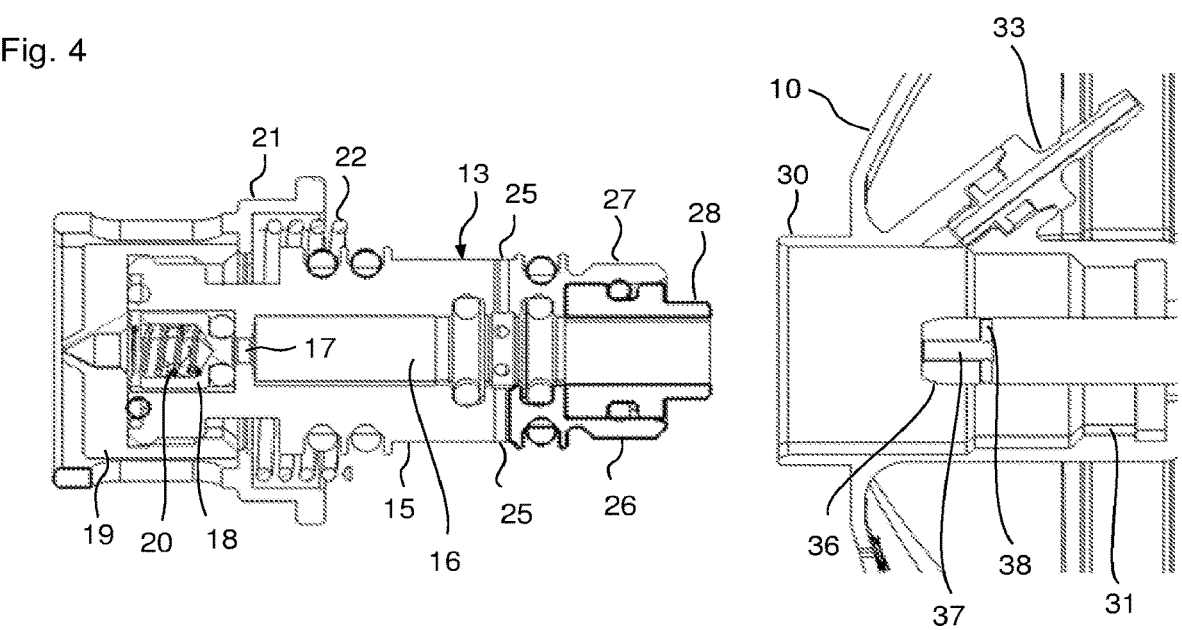
FIG. 4 shows a schematic sectional view of the first front assembly 13 and of the distal end 30 of the receiving block 10 in a state not connected to each other.
Figure 5:
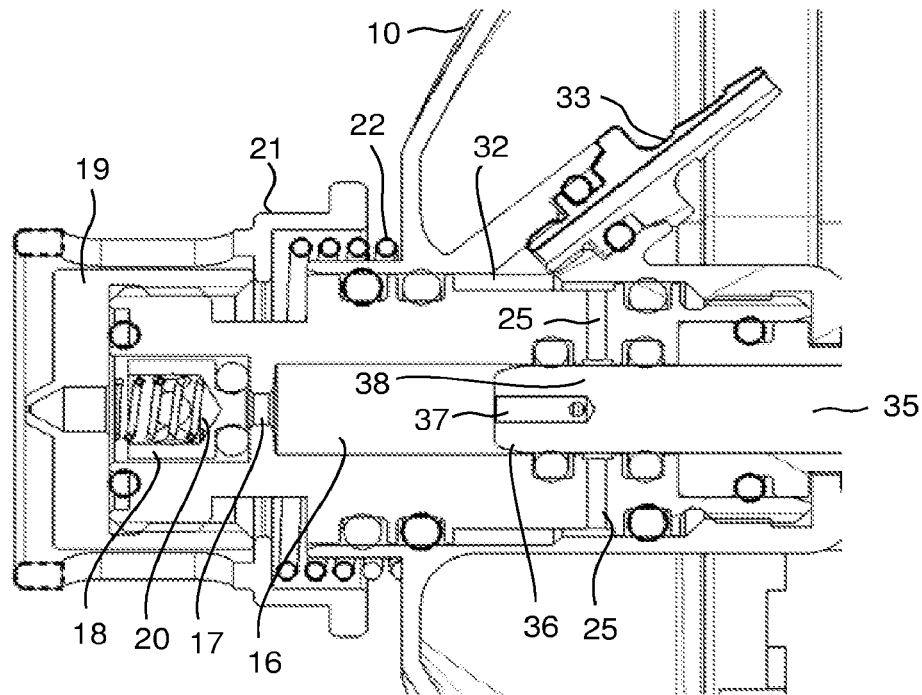
FIG. 5 shows a schematic sectional view of the first front assembly 13 screwed into the distal end of the receiving block 10, with the piston 36 being in its rear end position.

An external thread 27 is formed, and a guide bushing 28 arranged, at the proximal end 26 of the front assembly 13, and therefore the front assembly 13 can be screwed into a distal end 30 of the receiving block 10 (FIG. 4) since an internal thread 31 for the external thread 27 of the front assembly 13 is provided in the distal end 30. FIG. 4 shows the front assembly 13 and the distal end 30 of the receiving block 10 prior to the screwing-in operation. In FIG. 5, the two elements 13, 30 are screwed to each other such that a piston rod 35 which is guided in the receiving block 10 slightly protrudes with a piston 36 formed at its distal end into the syringe cylinder 16, and the piston rod 35 is guided through the guide bushing 28. As will be described in detail below, the piston rod 35 can be moved from the basic position shown in FIG. 5 in the direction toward the open dispensing end 17 to the injection or dispensing position shown in FIG. 6 and from said position back again into the basic position shown in FIG. 5.

If the piston rod 35 is in the basic position, its distal end and therefore the piston 36 is in its rear end position (FIG. 5). When the piston rod 35 is in the dispensing position, the piston 36 is in its front end position (FIG. 6).

When the piston rod 35 is positioned in the basic position shown in FIG. 5, the syringe cylinder 16 is filled with the liquid drug to be injected. A movement of the piston rod 35 toward the open dispensing end 17 then leads to the nonreturn valve 18 opening and thus to the liquid being dispensed via the nozzle 19 as a jet which cuts into the skin of the animal to an extent such that the drug can be administered into the skin through said cut.

Figure 6:
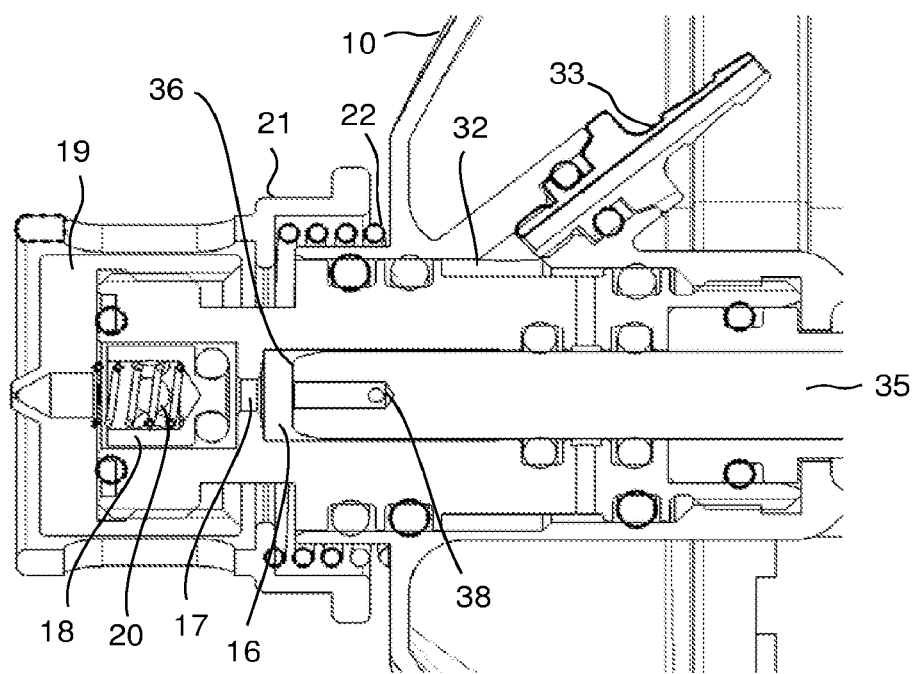
FIG. 6 shows a sectional view according to FIG. 5, wherein the piston 36 is in its front end position and the triggering cage 21 is in its release position for the administering operation.

During the rearward movement from the dispensing position shown in FIG. 6 to the basic position shown in FIG. 5 (a movement along a first direction), the nonreturn valve 18 closes and a negative pressure is produced in the syringe cylinder 16, said negative pressure being greater the further the piston rod 35 is moved away from the open dispensing end 17. As soon as the piston rod 35 is brought into its basic position, there is a fluid connection between the syringe cylinder 16 and at least one of the supply channels 25. In order to realize the fluid connection, an axial blind hole 37 is formed in the distal end of the piston 36 and at least one transverse bore 38 is formed which extends radially from the blind bore 37 and the end of which that faces away from the blind bore 37 leads into one of the supply channels 25. Since the supply channels 25 for their part lead into a chamber 32 which is formed between the insert 15 and the distal end 30 of the receiving block 10 and is connected via a connection element 33 to the medication container M, only shown in FIG. 2, the liquid drug because of the negative pressure present in the syringe cylinder 16 is sucked out of the medication container M via the connection element 33, the chamber 32, the supply channel or supply channels 25, the transverse bore(s) 38 and the blind bore 37 into the syringe cylinder 16 such that the latter is filled with the liquid drug. Therefore, the drug can be administered again during the next triggering operation, wherein, at the beginning of the movement of the piston rod 35 from the basic position to the injection position, some of the liquid drug is pressed back into the chamber 32 via the supply channels 25. This pressing back is advantageous since the piston 36 or the piston rod 35 can thereby be accelerated more easily, which leads to a higher pressure with which the rest of the drug in the syringe cylinder 16 is acted upon and which is desirable for the described injection without a needle.

The front assembly 13 which in particular comprises the syringe cylinder 16, the nonreturn valve 18 and the nozzle 19 is designed to be exchangeable as a whole. It can be screwed by means of its external thread 27 into, and unscrewed again from, the corresponding internal thread 31 which is formed at the distal end 30 of the receiving block 10. Since the front assembly 13 is subject to wear during operation of the administering device 1, a worn front assembly 13 can therefore be easily exchanged for a new, structurally identical front assembly 13. This advantageously leads to the administering device 1 as a whole being able to be used for longer since the components of the administering device 1 that are most susceptible to wear can be easily exchanged.

Since the front assembly 13 can be completely exchanged, undesirable contaminations can be reliably avoided, which would be significantly more difficult to avoid and would be associated with higher costs if, for example, the firstly wearing O-ring seals in the administering devices known from the art were individually exchanged in the region of the cylinder which is connected fixedly and nonexchangeably to the rest of the device known from the art.

Figure 7:
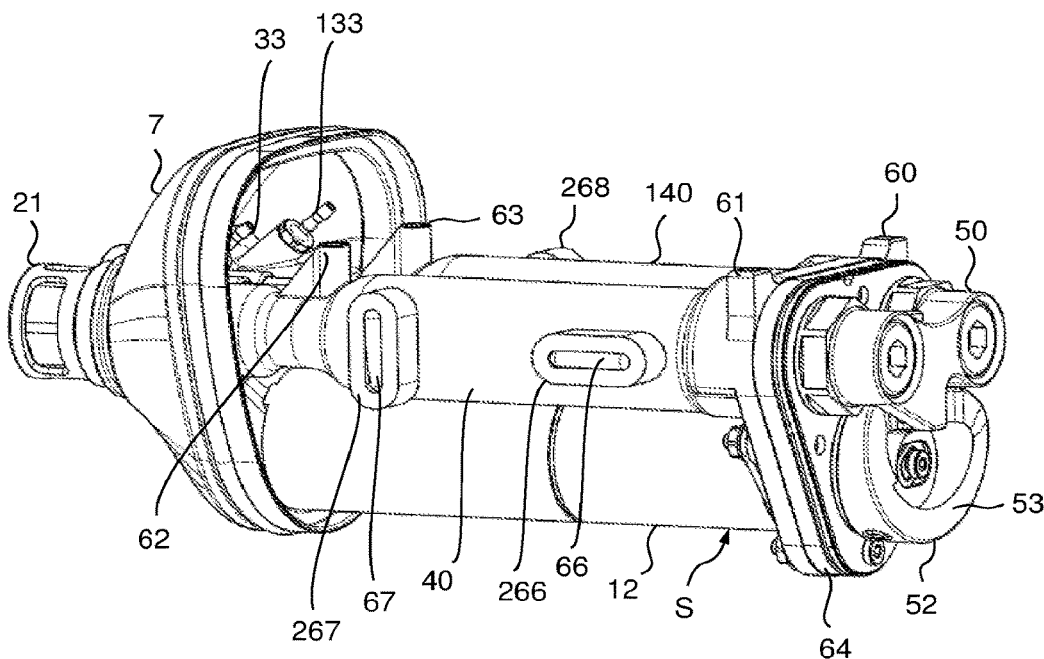
FIG. 7 shows a perspective illustration of the receiving block 10 together with the tensioning device S, wherein the tensioning device S is in the basic position in which the piston 36 is in its front end position.
Figure 8:
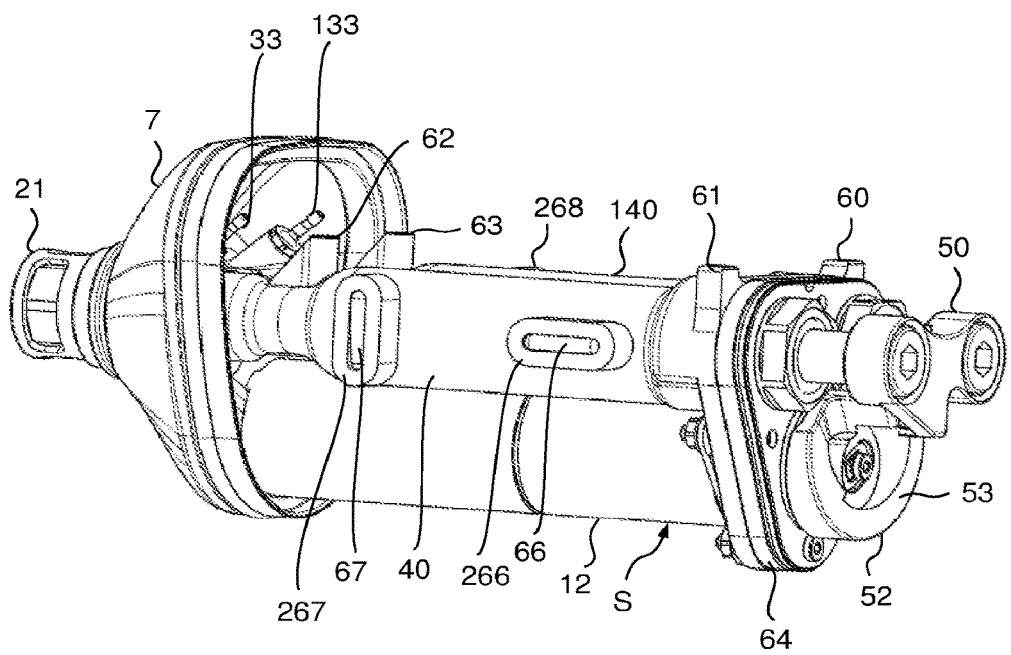
FIG. 8 shows a perspective illustration of the receiving block 10 together with the tensioning device S according to FIG. 7, wherein the tensioning device S is in its tensioned position in which the piston 36 is in its rear end position.
Figure 9:
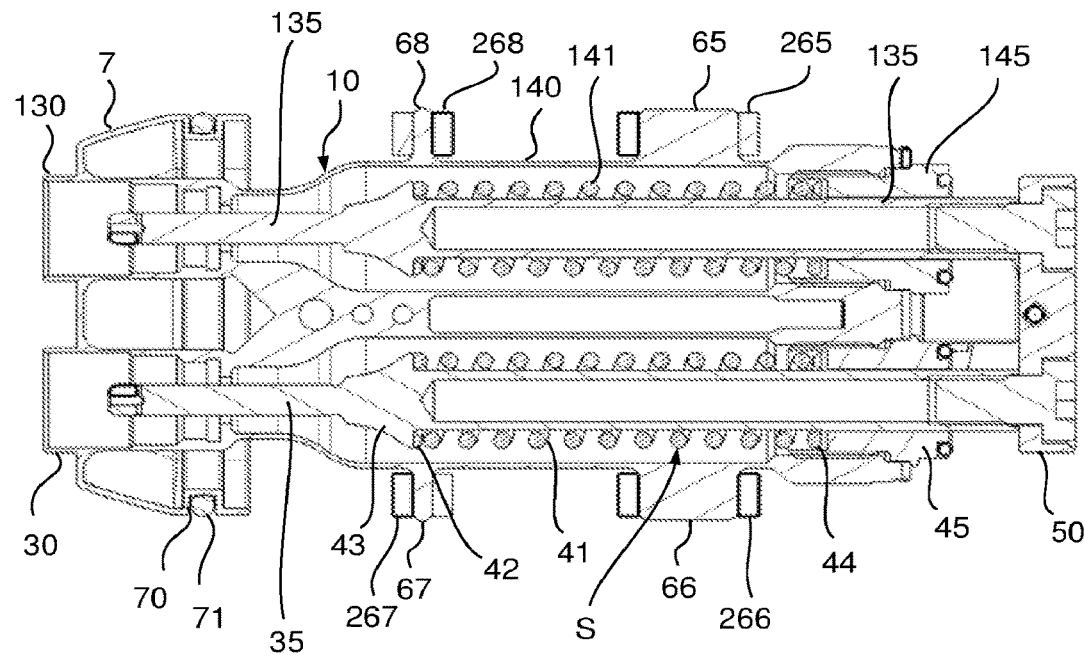
FIG. 9 shows a sectional view of the receiving block 10 together with the tensioning device S according to FIG. 8.

As can best be seen from FIGS. 7 to 9, the receiving block 10 has a first receiving cylinder 40, into which the piston rod 35 for the first front assembly 13 is guided, and a second receiving cylinder 140, in which a piston rod 135 for the second front assembly 14 is guided. Since the construction of the two cylinder-piston arrangements and therefore of the two receiving cylinders 40, 140 is identical, essentially only the first cylinder-piston arrangement with the first receiving cylinder 40 will be described below in the description of the receiving block 10. Corresponding elements in the case of the second receiving cylinder 140 are denoted by reference signs which are greater by 100 than in the case of the elements of the first receiving cylinder 40 but will not be described once again.

The piston rod 35 runs through the first receiving cylinder 40 in which a spring 41 for moving the piston rod 35 from the tensioned basic position shown in FIG. 5 to the injection position shown in FIG. 6 is contained. A distal end 42 of the spring 41 lies against a stop portion 43 of the piston rod 35. The proximal end 44 of the spring 41 lies against a guide bushing 45 which is screwed into the proximal end of the first receiving cylinder 40, and therefore, during a movement of the piston rod from the injection position shown in FIG. 6 along the first direction to the pretensioned basic position shown in FIG. 5, the spring 41 is compressed and is thereby pretensioned, as is illustrated in FIG. 9.

Figure 10:
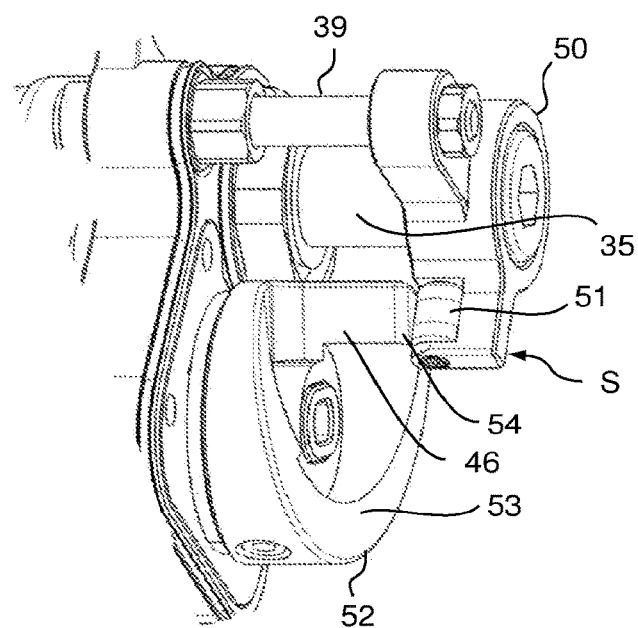
FIG. 10 shows a perspective enlarged detailed illustration of the rear part of the tensioning device S with the roller 51 and ramp 52 of a modification of the administering device 1 according to the invention with just one cylinder-piston arrangement.

As can be gathered in particular from the enlarged perspective illustration in FIG. 10, that end of the piston rod 35 which protrudes proximally out of the receiving cylinder 40 is connected to a driver 50 which has a rotatably mounted roller 51, wherein the axis of rotation of the roller 51 extends substantially perpendicularly to the longitudinal axis of the piston rod 35.

The perspective illustration in FIG. 10 shows a modification of the administering device 1 according to the invention. In this modification, only a single cylinder-piston arrangement is formed, and the driver 50 is connected to the proximal end of the piston rod 35 and to the proximal end of a guide rod 39, which is mounted displaceably in the receiving block 10.

The roller 51 runs on a ramp 52 which rotates under the roller 51 and is rotated by the motor 12 about an axis parallel to the longitudinal axis of the piston rod 35. A battery and/or a storage battery which can be recharged is provided as current supply for the motor. The battery and/or the storage battery can be arranged, for example, in the base 3 or as the base 3 of the administering device 1.

The ramp 52 has a ramp track 53 which runs with a single turn along a helical line, as can be gathered in particular from FIGS. 7, 8 and 10.

Figure 11A:
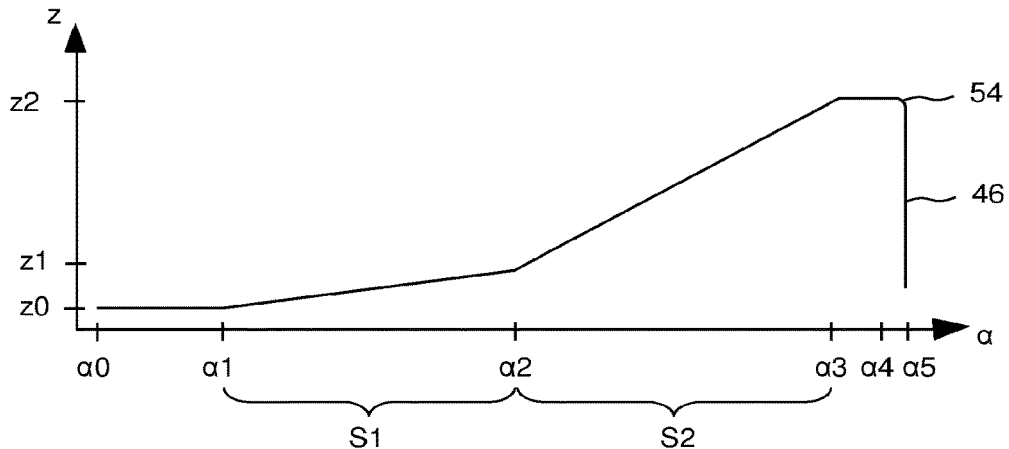
FIG. 11A shows a diagram for illustrating the profile of the ramp track 53, wherein the angle of rotation is plotted along the x axis and the stroke along the longitudinal axis of the piston rod 36 is plotted along the y axis.

In FIG. 11A, the angle of rotation $\alpha$ is plotted in relation to the pitch difference z parallel to the longitudinal direction of the piston rod 35, wherein the starting point is that, at the angle of rotation of $\alpha 0=0°$, the smallest pitch height z0 is present and the piston 36 is in its front end position. If the ramp 52 is then rotated, the ramp track 53 runs under the roller 51 and leads to the rotational movement of the ramp track 53 being converted into a translatory movement of the roller 51 together with the driver 50 and therefore the piston rod 35 along the longitudinal axis of the piston rod 35, such that the piston rod 35 is moved from its injection position shown in FIG. 6 into its basic position shown in FIG. 5.

For this purpose, the unwound ramp track 53 according to FIG. 11A runs in such a manner that there is a first plateau (inclination=0 or only somewhat greater or somewhat less than zero) from the angle of rotation $\alpha 0$ to an angle of rotation $\alpha 1$. From the angle of rotation $\alpha 1$, the ramp track 53 has a first linear inclination portion S1 which is present as far as the angle of rotation $\alpha 2$. At the angle of rotation $\alpha 2$ (and the corresponding pitch height z1), the pitch merges into a second linear inclination portion S2 which has a greater inclination than the first linear inclination portion S1 (between the angles of rotation $\alpha 1$ and $\alpha 2$). The second inclination is present as far as the angle of rotation $\alpha 3$ and then merges into a second plateau in which the pitch height z2 does not increase (or only increases very slightly or only decreases very slightly) in the event of a further increase in the angle of rotation as far as the angle of rotation $\alpha 4$ of less than 360°.

At the angle of rotation $\alpha 5$, an edge 54 is formed because of the transition flank 46 which connects the second plateau to the first plateau.

In the region from $\alpha 3$ to $\alpha 4$, the piston rod 35 is in its tensioned basic position according to FIG. 5. The administering device 1 is therefore ready for the application of the liquid drug.

If the trigger 5 is then actuated and the triggering cage 21 is in the triggering position, the motor 12 rotates the ramp 52 further such that, when the angle of rotation $\alpha 5$ is exceeded, the roller 51 runs over the edge 54 and, because of the tensioning of the spring 41, drops abruptly back from the pitch height z2 to the pitch height z0 of the first plateau, and therefore the fluid present in the syringe cylinder 16 is injected in the described manner.

The motor 12 then rotates the ramp 52 further as far as the second plateau and stops the rotational movement here such that the syringe cylinder 16 is thereby again filled with the liquid drug and the piston rod 35 is brought again into its tensioned basic position. The administering device 1 is therefore provided for a further administering operation. The administering device 1 can thereby be repeatedly wound up and triggered.

The two inclination portions S1 and S2 form a region of inclination which runs from the first plateau as far as the second plateau. The two inclination portions S1 and S2 do not have to run linearly with respect to the angle of rotation. As is shown by way of example in FIG. 11B, they can also have a concave curvature (at which the local inclination increases as the angle of rotation increases). However, even in this case, the average inclination of the first inclination portion S1 is smaller than the average inclination of the second inclination portion S2.

The combination of motor 12, ramp 52, driver 50 with roller 51, spring 41, 141 and guide bushing 45, 145 can be referred to as the tensioning device S.

Figure 12:
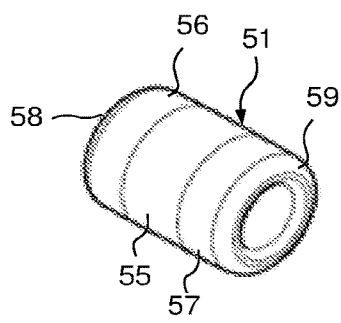
FIG. 12 shows a perspective illustration of the roller 51.
Figure 13:
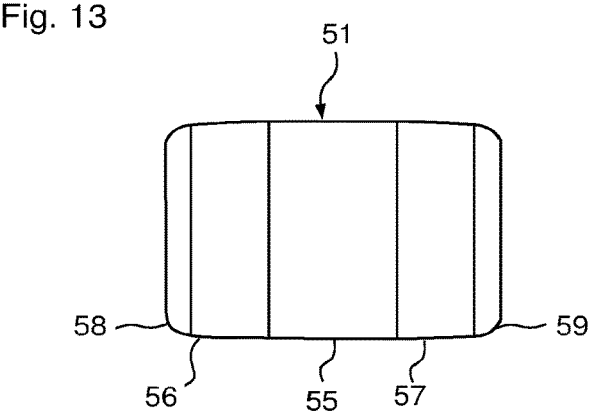
FIG. 13 shows a top view of the roller 51.
Figure 14:
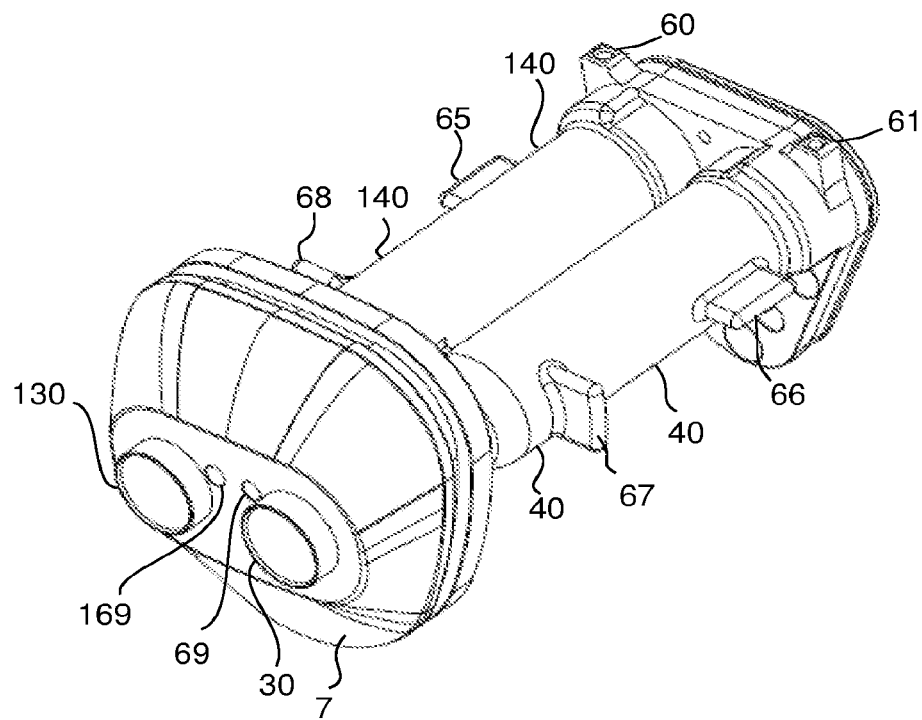
FIGS. 14 and 15 show perspective illustrations of the receiving block 10.
Figure 15:
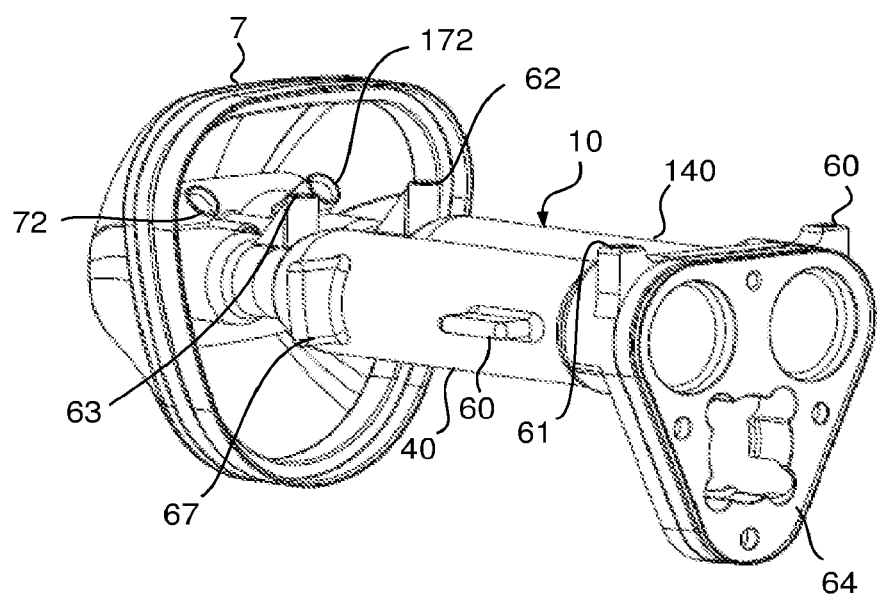
Figure 16:
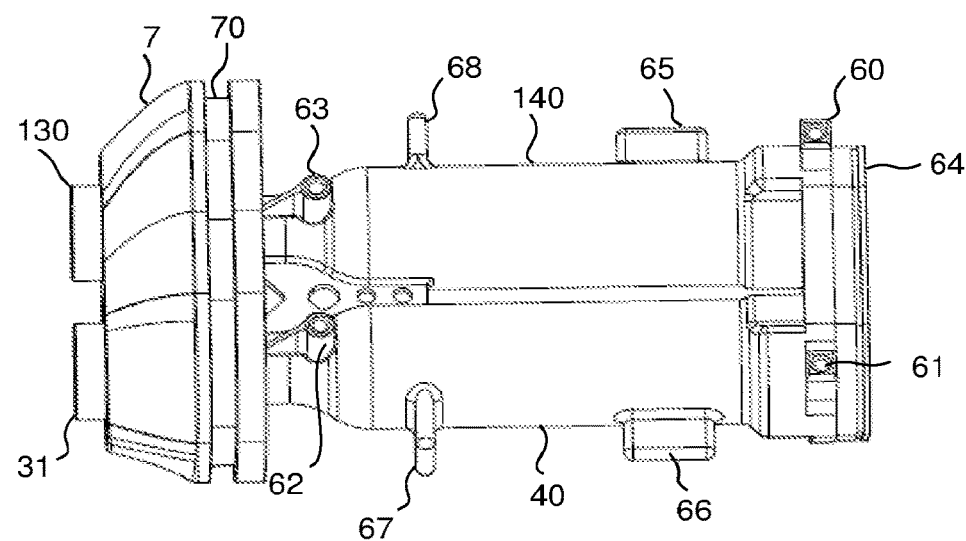
FIG. 16 shows a top view of the receiving block 10.
Figure 17:
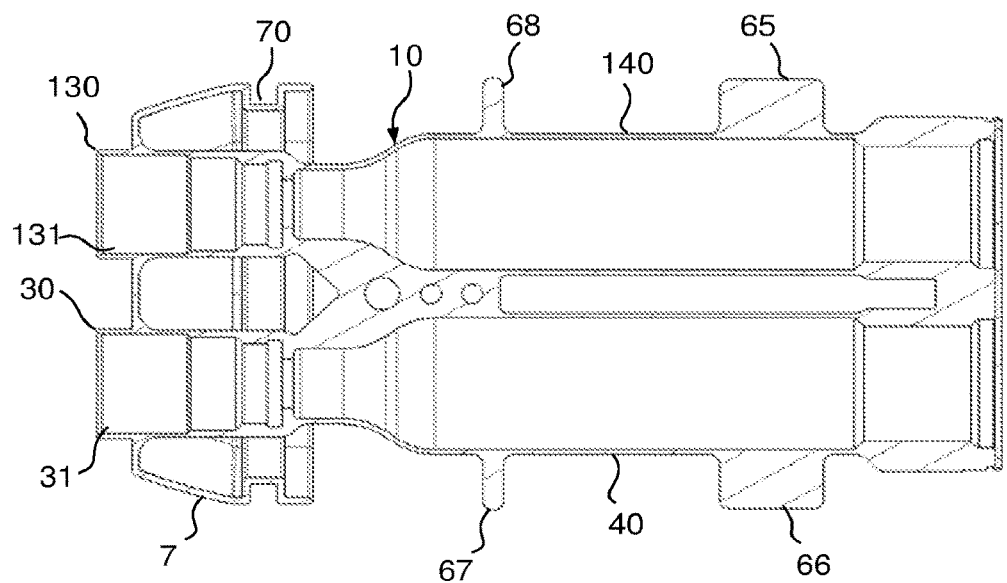
FIG. 17 shows a sectional view of the receiving block 10.

As can be gathered in particular from FIGS. 12 and 13, the roller 51 comprises a central region 55 which has a constant outside diameter. This is adjoined on both sides by a respective side region 56, 57 in which the outside diameter decreases toward the side.

The two side regions 56 and 57 are each adjoined by an end region 58, 59 which is rounded so that the roller 51 does not have any edges. Upon rotation of the ramp 52, the central region 55 lies on the ramp track 53 in the rotational angle region of $\alpha 1$ to $\alpha 3$ (in particular of $\alpha 0$ to $\alpha 5$) whereas the side regions 56 and 57 do not rest in said rotational angle region, but rather come into contact with the ramp track 53 only on running over the edge 54. The rolling resistance of the roller 51 during the tensioning of the piston rod 35 (rotation of the ramp track from the first to the second plateau) can therefore be as small as possible. During the transfer from the second or upper plateau (rotational angle region $\alpha 3$ to $\alpha 4$) of the ramp track 53 to the lower plateau (rotational angle region $\alpha 1$ to $\alpha 2$), the side regions 56 and 57 are also in contact with the edge 54, as a result of which the forces between the roller 51 and the edge 54 of the ramp track 52 are advantageously distributed over a greater support surface (central region 55 and the two side regions 56, 57), and therefore a smaller pressure is present. The durability of the device 1 and in particular of the roller 51 is thereby increased.

Figure 11B:
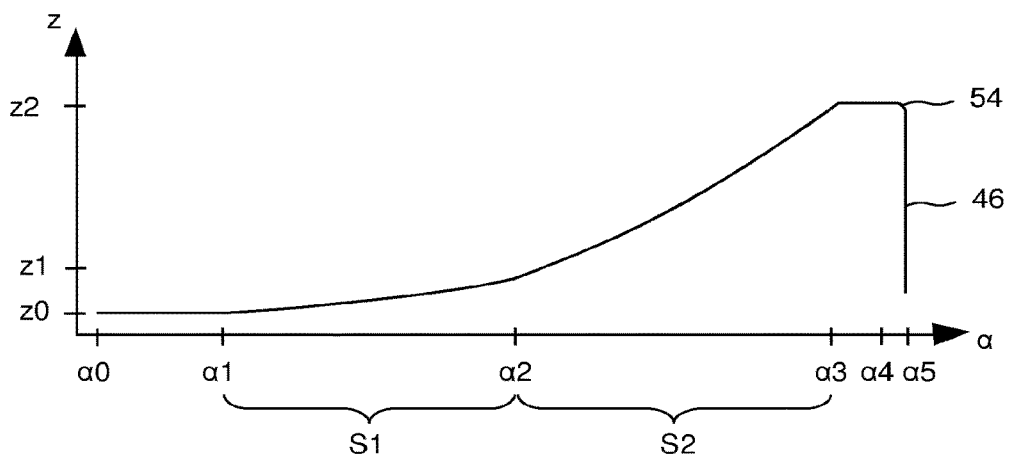
FIG. 11B shows a diagram for illustrating the modified profile of the ramp track 53, wherein the angle of rotation is plotted along the x axis and the stroke along the longitudinal axis of the piston rod 36 is plotted along the y axis.

The characteristics of the inclination of the ramp track 53 described in conjunction with FIGS. 11A and 11B are advantageous since, at the beginning (rotational angle region α1 to α2), there is a smaller inclination, and therefore less torque has to be provided by the motor 50. This is of advantage precisely during the starting of the motor 50 from the first plateau since the motor 50 customarily draws more current in this region. When the pitch height z1 is reached, the higher inclination in the rotational angle region from α2 to α3 can easily be overcome by the motor 50.

These characteristics of the inclination of the ramp track 52 advantageously lead to the durability of the motor 50 being increased.

As can best be gathered from the illustrations from FIGS. 14 to 17, the receiving block 10 is formed integrally. Here, for example, use has been made of an additive production method, such as, for example, laser sintering, selective laser sintering or direct metal laser sintering, with which finer and/or more complex structures can be produced in comparison to machining methods. The receiving block 10 can therefore be provided with a relatively low weight and it can be ensured that the administering device 1 is highly durable.

Examples of the material used for the receiving block 10 can include aluminum, steel (for example maraging steel), stainless steel, titanium, a nickel alloy and/or a cobalt chromium alloy. The material for the laser sintering here is preferably in the form of metal powder. For the additive or layered production of the receiving block 10, a thin layer of the powder material can be applied to a construction platform. A laser beam melts the powder exactly at the points which are predetermined by computer-generated component design data of the receiving block 10. The construction platform is then lowered, and a further thin layer of the powder material is applied. The material is melted again and binds at the defined points to the layer lying therebelow. These steps are repeated until the entire receiving block 10 is formed.

In addition to the receiving cylinders 40, 140 already described, the receiving block 10 comprises four board receiving points 60, 61, 62 and 63, onto which the board 11 can be placed and, for example, screwed to the receiving block 10.

Furthermore, the receiving block comprises a motor bearing 64 for receiving and mounting the motor 12.

Furthermore, four fixation points 65, 66, 67 and 68 are formed for the outer housing 2 of the administering device 1. Portions of corresponding receptacles 265, 266, 267 and 268 of the outer housing 2 are shown in FIGS. 7 to 9.

At the distal end of the receiving block 10, the umbrella-like dispensing region 7 is provided which, in addition to the corresponding internal thread 31 and 131 for the first and second front assembly 13 and 14, also has receptacles 69 and 169 for the respective triggering sensor (not shown) that detects the position of the triggering cage 21, 121.

Furthermore, an O-ring receptacle 70, into which an O-ring 71 (for example FIGS. 9, 16 and 17) can be inserted, is formed in the dispensing region 7 in order to ensure sealing in relation to the adjacent housing 2 in the installed state.

Furthermore, the receiving block 10 for each receiving cylinder 40, 140 comprises a receptacle 72, 172, into which the corresponding connection element 33, 133, which can also be referred to as a fluid adapter, can be inserted.

The connection element 33, 133 is preferably produced by machining.

Titanium is preferably used as the material for the receiving block 10. This material is firstly relatively light and secondly ensures the desired strength. Of course, any other suitable material for additive production methods may be used.

The description above has been based on the intention of simultaneously administering two different medications. However, the administering device 1 according to the invention may also be designed in such a manner that the receiving block 10 has only one individual receiving cylinder 40, and therefore also only one single medication can be administered during a triggering operation. The second receiving cylinder 140 and the second cylinder-piston rod combination are then preferably omitted.

The previously described exemplary embodiments have been based on the administering device 1 being in the form of an administering device 1 without needles. However, it may also be in the form of an administering device 1 with a needle or a canula, and therefore, in this case, the needle or canula is intended to pierce the skin of the animal and then the application of the liquid drug takes place in the described manner.

What is claimed is:

1. A device for administering a fluid, comprising
a cylinder (16, 116) which has an open dispensing end (17),
a piston (36) which is displaceable between a front and rear end position in the cylinder (16, 116) and is connected to a plunger rod (35) that protrudes along a first direction beyond a rear end of the cylinder (16, 116) opposite the open dispensing end (17) and is guided in a receiving block (10),
a nonreturn valve (18) closing the open dispensing end (17), and
a tension device(S) which is connected to the piston rod (35, 135) and is arranged in the receiving block (10),
wherein the tensioning device(S), when the piston (36) is in its front end position, can move the piston rod (35, 135) in a tensioning operation along the first direction until the piston (36) is in its rear end position in order thereby to fill the cylinder (16, 116) with the fluid to be administered and in order to pretension the piston rod (35, 135) toward the open dispensing end (17), and
wherein the tensioning device(S), when the piston (36) is in its rear end position, can release the piston rod (35, 135) in a dispensing operation, and therefore the piston (36) moves counter to the first direction as far as its front end position because of the applied pretension and, in the process, fluid in the cylinder (16, 116) is dispensed via the nonreturn valve (18) for administering,
the tensioning device(S) has a ramp (52) which is rotatable by means of a motor (12) and has a ramp track (53) extending along a helical line;
wherein the ramp track (53) ascends from a first level along a region of inclination to a second level and descends from the second level to the first level via a transition flank (46),
wherein the tensioning device(S) furthermore has a roller (51) which is in contact with the ramp track (53) and is mounted rotatably in a driver (50), which is connected to that end of the piston rod (35, 135) which protrudes out of the cylinder (16, 116), and therefore, upon rotation of the ramp (52), the ramp track (53) runs below the roller (51), which thereby rotates, wherein, for the tensioning operation, the ramp track (53), is rotated in such a manner that the roller (51) rolls on the ramp track (53) from the first level, along the region of inclination, to the second level and the piston (36) is thereby moved into its rear end position, wherein, for the dispensing operation, the ramp track (53) is rotated in such a manner that the roller (51) via the transition flank (46) reaches the first level and the piston (36) is thereby moved into its front end position.

2. The device as claimed in claim 1, wherein the roller (51) has a support region (55) which rests on the region of inclination of the ramp track (53), and at least one laterally adjoining side region (56, 57) which has a smaller outside diameter than the support region (55) and which does not rest on the region of inclination of the ramp track (53).

3. The device as claimed in claim 2, wherein, during the dispensing operation, both the support region (55) and the side region (56, 57) come into contact with an edge (54) of the ramp track (53), said edge connecting the second level to the transition flank (46).

4. The device as claimed in claim 2, wherein the outside diameter of the respective side region (56, 57) decreases in a direction toward the side of the roller (51).

5. The device as claimed in claim 1, wherein the roller (51) is mounted in the driver (50) in such a manner that the axis of rotation of said roller is perpendicular to the first direction.

6. The device as claimed in claim 1, wherein the cylinder (16, 116) together with the nonreturn valve (18) is in the form of an exchangeable front assembly (13, 14) which is releasably connected to the receiving block (10).

7. The device as claimed in claim 6, wherein the releasable connection between the front assembly (13, 14) and the receiving block (10) is a screw connection.

8. The device as claimed in claim 6, wherein the device has a nozzle (19) for administering the fluid without a needle, said nozzle being connected to the open dispensing end of the cylinder (16, 116) via the nonreturn valve (18) and being part of the front assembly (13, 14).

9. The device as claimed claim 1, wherein the tensioning device(S) has a spring (41, 141) which pretensions the piston rod (35, 135) toward the open dispensing end when the piston rod (36) is in the rear end position.

10. The device as claimed claim 1, wherein the motor (12) is mounted in the receiving block (10).

11. The device as claimed in claim 1, wherein the region of inclination of the ramp track (53) has a first portion (S1) adjoining the first plateau and an adjoining second portion (S2), wherein the inclination of the second portion (S2) is greater than the inclination of the first portion (S1).

12. The device as claimed in claim 11, wherein both portions (S1, S2) run linearly with respect to the angle of rotation of the helical line.

13. The device as claimed in claim 11, wherein at least one of the two portions (S1, S2) does not run linearly with respect to the angle of rotation of the helical line.

14. The device as claimed in claim 11, wherein the length of the angle of rotation of the first portion (S1) is smaller than the length of the angle of rotation of the second portion (S2).

15. The device as claimed claim 1, in which the receiving block (10) is in the form of an integral receiving block (10) which is produced by an additive production method.

16. The device as claimed in claim 15, wherein the receiving block (10) is in the form of a metal receiving block (10).

17. The device as claimed in claim 15, wherein the receiving block (10) has a motor bearing (64), a guide cylinder (40, 140) for the piston rod (35, 135), at least one receptacle (60, 61, 62, 63) for a control board (11), a receptacle (72, 172) for a fluid connection (33) for a fluid container (M) and/or at least one housing fixing point (65, 66, 67, 68), which are/is formed integrally with the receiving block (10).

18. The device as claimed in claim 1, wherein the first level of the ramp track includes a first plateau.

19. The device as claimed in claim 1, wherein the second level of the ramp track includes a second plateau.

* * * * *

UNITED STATES PATENT AND TRADEMARK OFFICE
CERTIFICATE OF CORRECTION

PATENT NO. : 12,201,815 B2
APPLICATION NO. : 18/057636
DATED : January 21, 2025
INVENTOR(S) : Frank Altermann et al.

Page 1 of 1

It is certified that error appears in the above-identified patent and that said Letters Patent is hereby corrected as shown below:

On the Title Page

Column 1 Item (63) Related U.S. Application Data, reads:
(63) Continuation-in-part of application No. 17/040,415, filed as application No. PCT/EP2019/057535 on Mar. 26, 2019, now Pat. No. 11,534,550.

This should be corrected to read:
(63) Continuation of application No. 17/040,415 filed September 22, 2020, now Pat. No. 11,534,550, a national phase entry of application No. PCT/EP2019/057535 filed Mar. 26, 2019.

Signed and Sealed this
Eleventh Day of March, 2025

Coke Morgan Stewart
*Acting Director of the United States Patent and Trademark Office*